US010568741B2

(12) United States Patent
Conway et al.

(10) Patent No.: US 10,568,741 B2
(45) Date of Patent: *Feb. 25, 2020

(54) IMPLANT COMPONENTS AND METHODS

(71) Applicant: Smith & Nephew, Inc., Memphis, TN (US)

(72) Inventors: Justin Steve Conway, Olive Branch, MS (US); Ryan L. Landon, Southaven, MS (US); Jeffrey Joel Shea, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 11 days.

This patent is subject to a terminal disclaimer.

(21) Appl. No.: 15/596,482

(22) Filed: May 16, 2017

(65) Prior Publication Data
US 2017/0246001 A1  Aug. 31, 2017

Related U.S. Application Data

(60) Continuation of application No. 14/191,600, filed on Feb. 27, 2014, now Pat. No. 9,707,083, which is a
(Continued)

(51) Int. Cl.
*A61F 2/34* (2006.01)
*G06F 9/455* (2018.01)
(Continued)

(52) U.S. Cl.
CPC ............ *A61F 2/34* (2013.01); *A61B 17/8066* (2013.01); *A61F 2/30734* (2013.01);
(Continued)

(58) Field of Classification Search
CPC .... A61F 2/34; A61F 2/30767; A61F 2/30771; A61F 2/30734; A61F 2/4609; A61F 2002/30011; A61F 2013/00778
See application file for complete search history.

(56) References Cited

U.S. PATENT DOCUMENTS 3,896,504 A   7/1975  Fischer
4,298,993 A  11/1981  Kovaleva et al.
(Continued)

FOREIGN PATENT DOCUMENTS

CN      1826147 A    8/2006
CN    101050053 A   10/2007
(Continued)

OTHER PUBLICATIONS

Australian Examination Report; Australian Patent Office; Australian Patent Application No. 2018200989; dated Oct. 15, 2018; 5 pages.
(Continued)

*Primary Examiner* — Alvin J Stewart

(57) ABSTRACT

Systems, devices, and methods are provided for orthopedic implants. The implants may include a base member, such as an acetabular shell or an augment, that is configured to couple with an augment, flange cup, mounting member, or any other suitable orthopedic attachment. Any of the implantable components may be include one or more porous surfaces. The porous surface may be textured by protrusions that connect to and extend from the surface. The sizes and concentration of the protrusions may be varied for specific applications to accommodate different implants and patient anatomies. A porous implant may also include one or more internal or external solid portions that strengthen the implant.

29 Claims, 3 Drawing Sheets

Related U.S. Application Data division of application No. 13/156,245, filed on Jun. 8, 2011, now Pat. No. 8,700,198.

(60) Provisional application No. 61/352,705, filed on Jun. 8, 2010, provisional application No. 61/352,722, filed on Jun. 8, 2010, provisional application No. 61/422,903, filed on Dec. 14, 2010, provisional application No. 61/466,817, filed on Mar. 23, 2011.

(51) Int. Cl.
| | | |
|---|---|---|
| *A61B 17/80* | (2006.01) | |
| *A61F 2/30* | (2006.01) | |
| *A61F 2/46* | (2006.01) | |
| *B33Y 80/00* | (2015.01) | |
| *A61B 17/82* | (2006.01) | |
| *A61B 17/86* | (2006.01) | |

(52) U.S. Cl.
CPC ...... *A61F 2/30749* (2013.01); *A61F 2/30771* (2013.01); *A61F 2/30965* (2013.01); *A61F 2/4609* (2013.01); *G06F 9/45533* (2013.01); A61B 17/82 (2013.01); A61B 17/866 (2013.01); A61B 17/8685 (2013.01); A61F 2/30907 (2013.01); A61F 2/30942 (2013.01); A61F 2002/30011 (2013.01); A61F 2002/30013 (2013.01); A61F 2002/3038 (2013.01); A61F 2002/3082 (2013.01); A61F 2002/3092 (2013.01); A61F 2002/3093 (2013.01); A61F 2002/3096 (2013.01); A61F 2002/30169 (2013.01); A61F 2002/30189 (2013.01); A61F 2002/30326 (2013.01); A61F 2002/30387 (2013.01); A61F 2002/30449 (2013.01); A61F 2002/30462 (2013.01); A61F 2002/30471 (2013.01); A61F 2002/30474 (2013.01); A61F 2002/30507 (2013.01); A61F 2002/30538 (2013.01); A61F 2002/30578 (2013.01); A61F 2002/30579 (2013.01); A61F 2002/30604 (2013.01); A61F 2002/30611 (2013.01); A61F 2002/30617 (2013.01); A61F 2002/30736 (2013.01); A61F 2002/30841 (2013.01); A61F 2002/30891 (2013.01); A61F 2002/30952 (2013.01); A61F 2002/30985 (2013.01); A61F 2002/348 (2013.01); A61F 2002/3412 (2013.01); A61F 2002/3429 (2013.01); A61F 2002/3441 (2013.01); A61F 2002/3448 (2013.01); A61F 2002/3487 (2013.01); A61F 2002/4615 (2013.01); A61F 2002/4619 (2013.01); B33Y 80/00 (2014.12)

(56) References Cited

U.S. PATENT DOCUMENTS

| | | | |
|---|---|---|---|
| 4,491,987 A | | 1/1985 | Park |
| 4,542,539 A | * | 9/1985 | Rowe, Jr. ............ A61F 2/30767 623/23.57 |
| 4,547,390 A | | 10/1985 | Ashman et al. |
| 4,589,883 A | * | 5/1986 | Kenna ................ A61F 2/36 606/62 |
| 4,883,491 A | | 11/1989 | Mallroy et al. |
| 4,904,265 A | | 2/1990 | MacCollum et al. |
| 5,041,140 A | | 8/1991 | Teinturier |
| 5,176,711 A | | 1/1993 | Grimes |
| 5,236,457 A | | 8/1993 | Devanathan |
| 5,236,462 A | * | 8/1993 | Mikhail .............. A61F 2/30767 623/20.2 |
| 5,246,530 A | * | 9/1993 | Bugle ................. B23K 26/08 216/56 |
| 5,326,368 A | | 7/1994 | Collazo |
| 5,370,698 A | * | 12/1994 | Heimke ............. A61F 2/30767 623/22.15 |
| 5,425,778 A | | 6/1995 | Zichner et al. |
| 5,441,527 A | | 8/1995 | Erickson et al. |
| 5,458,637 A | | 10/1995 | Hayes |
| 5,458,641 A | * | 10/1995 | Ramirez Jimenez ..... A61F 2/44 403/43 |
| 5,507,748 A | | 4/1996 | Sheehan et al. |
| 5,531,793 A | | 7/1996 | Kelman et al. |
| 5,549,685 A | | 8/1996 | Hayes |
| 5,607,480 A | * | 3/1997 | Beaty ................. A61C 8/0012 623/23.5 |
| 5,658,338 A | | 8/1997 | Tullos et al. |
| 5,658,347 A | | 8/1997 | Sarkisian et al. |
| 5,725,587 A | | 3/1998 | Garber |
| 5,871,548 A | | 2/1999 | Sanders et al. |
| 5,906,234 A | * | 5/1999 | Mastrorio ........... A61F 2/30771 164/45 |
| 6,087,553 A | * | 7/2000 | Cohen .................. C08L 23/06 623/22.21 |
| 6,096,083 A | * | 8/2000 | Keller ..................... A61F 2/34 623/18.11 |
| 6,162,257 A | | 12/2000 | Gustilo et al. |
| 6,193,761 B1 | | 2/2001 | Treacy |
| 6,209,621 B1 | | 4/2001 | Treacy |
| 6,210,715 B1 | * | 4/2001 | Starling ............. B01J 20/28019 423/308 |
| 6,231,612 B1 | | 5/2001 | Balay et al. |
| 6,280,476 B1 | | 8/2001 | Metzger et al. |
| 6,340,370 B1 | | 1/2002 | Willert et al. |
| 6,364,910 B1 | | 4/2002 | Shultz et al. |
| 6,416,553 B1 | | 7/2002 | White et al. |
| 6,458,161 B1 | | 10/2002 | Gibbs et al. |
| 6,488,713 B1 | | 12/2002 | Hershberger |
| 6,500,208 B1 | | 12/2002 | Metzger et al. |
| 6,811,569 B1 | | 11/2004 | Afriat et al. |
| 6,840,959 B2 | | 1/2005 | Treacy et al. |
| 6,908,486 B2 | | 6/2005 | Lewallen |
| 6,916,340 B2 | | 7/2005 | Metzger et al. |
| 7,014,633 B2 | | 3/2006 | Cragg |
| 7,044,974 B2 | | 5/2006 | Garber et al. |
| 7,179,297 B2 | | 2/2007 | McLean |
| 7,179,298 B2 | | 2/2007 | Greenlee |
| 7,291,177 B2 | | 11/2007 | Gibbs |
| 7,306,629 B2 | * | 12/2007 | Saladino ............... A61F 2/3609 623/22.42 |
| 7,371,261 B2 | | 5/2008 | Roger |
| 7,406,775 B2 | | 8/2008 | Funk et al. |
| 7,468,075 B2 | | 12/2008 | Lang et al. |
| 7,547,327 B2 | | 6/2009 | Collazo |
| 7,547,328 B2 | | 6/2009 | Sidebotham |
| 7,555,332 B2 | | 6/2009 | Rice et al. |
| 7,597,715 B2 | * | 10/2009 | Brown ..................... A61F 2/34 623/22.12 |
| 7,621,962 B2 | | 11/2009 | Lakin et al. |
| 7,635,447 B2 | | 12/2009 | Hamman et al. |
| 7,651,501 B2 | | 1/2010 | Penenberg et al. |
| 7,662,183 B2 | | 2/2010 | Haines |
| 7,713,306 B2 | | 5/2010 | Gibbs |
| 7,766,969 B2 | | 8/2010 | Justin et al. |
| 7,780,739 B2 | | 8/2010 | Lakin et al. |
| 7,922,769 B2 | | 4/2011 | Deffenbaugh et al. |
| 7,923,020 B2 | | 4/2011 | King et al. |
| 8,348,978 B2 | | 1/2013 | Trieu et al. |
| 8,383,187 B2 | * | 2/2013 | Rivard ................. A61F 2/30767 427/2.26 |
| 8,700,198 B2 | * | 4/2014 | Conway ............. A61B 17/8066 700/98 |
| 9,707,083 B2 | * | 7/2017 | Conway ............. A61B 17/8066 |
| 10,034,756 B2 | * | 7/2018 | Landon .................. A61F 2/389 |
| 10,052,184 B2 | * | 8/2018 | Deichmann .......... A61F 2/0063 |
| 2001/0037156 A1 | | 11/2001 | Burstein et al. |
| 2001/0039454 A1 | * | 11/2001 | Ricci ................... A61B 17/68 623/23.5 |
| 2001/0053913 A1 | | 12/2001 | Freedland |
| 2002/0042654 A1 | | 4/2002 | Masini |

(56) References Cited

U.S. PATENT DOCUMENTS

| | | | |
|---|---|---|---|
| 2002/0077661 A1* | 6/2002 | Saadat | A61B 17/08 606/221 |
| 2003/0009234 A1 | 1/2003 | Treacy et al. | |
| 2003/0045885 A1 | 3/2003 | Margulies et al. | |
| 2003/0065397 A1 | 4/2003 | Hanssen et al. | |
| 2003/0114935 A1 | 6/2003 | Chan et al. | |
| 2003/0171818 A1 | 9/2003 | Lewallen | |
| 2003/0212459 A1 | 11/2003 | Gibbs | |
| 2004/0024340 A1 | 2/2004 | Schwenn et al. | |
| 2004/0133276 A1 | 7/2004 | Lang et al. | |
| 2004/0199258 A1 | 10/2004 | Macara | |
| 2004/0225369 A1 | 11/2004 | Lakin et al. | |
| 2004/0225371 A1 | 11/2004 | Roger | |
| 2005/0021148 A1 | 1/2005 | Gibbs | |
| 2005/0149198 A1 | 7/2005 | Hawkins | |
| 2005/0171614 A1 | 8/2005 | Bacon | |
| 2005/0234561 A1 | 10/2005 | Nutt et al. | |
| 2005/0240276 A1 | 10/2005 | Shea et al. | |
| 2005/0246027 A1 | 11/2005 | Metzger et al. | |
| 2005/0267586 A1 | 12/2005 | Sidebotham | |
| 2005/0288793 A1 | 12/2005 | Dong et al. | |
| 2006/0178750 A1 | 8/2006 | Chieng | |
| 2006/0190080 A1* | 8/2006 | Danoff | A61F 2/30721 623/17.11 |
| 2006/0241776 A1 | 10/2006 | Brown et al. | |
| 2006/0282166 A1 | 12/2006 | Molz et al. | |
| 2007/0088443 A1 | 4/2007 | Hanssen et al. | |
| 2007/0129809 A1* | 6/2007 | Meridew | A61F 2/30721 623/22.32 |
| 2007/0142922 A1 | 6/2007 | Lewis et al. | |
| 2007/0179627 A1 | 8/2007 | Gustilo et al. | |
| 2007/0179629 A1 | 8/2007 | Murphy | |
| 2007/0198022 A1 | 8/2007 | Lang et al. | |
| 2007/0203584 A1* | 8/2007 | Bandyopadhyay | A61F 2/28 623/23.5 |
| 2007/0225813 A1 | 9/2007 | Haines | |
| 2007/0255412 A1* | 11/2007 | Hajaj | A61F 2/38 623/17.11 |
| 2008/0021568 A1 | 1/2008 | Tulkis et al. | |
| 2008/0040691 A1 | 2/2008 | Lee et al. | |
| 2008/0065154 A1 | 3/2008 | Allard et al. | |
| 2008/0088530 A1 | 4/2008 | Kang | |
| 2008/0125866 A1 | 5/2008 | McLean | |
| 2008/0161927 A1 | 7/2008 | Savage et al. | |
| 2008/0208353 A1* | 8/2008 | Kumar | A61F 2/30965 623/23.56 |
| 2008/0221680 A1 | 9/2008 | Hodorek | |
| 2008/0255568 A1 | 10/2008 | Tornier et al. | |
| 2008/0312741 A1 | 12/2008 | Lee et al. | |
| 2009/0088865 A1 | 4/2009 | Brehm | |
| 2009/0093887 A1 | 4/2009 | Walter et al. | |
| 2009/0204225 A1 | 8/2009 | Meridew et al. | |
| 2009/0240256 A1 | 9/2009 | Smith | |
| 2009/0292365 A1 | 11/2009 | Smith et al. | |
| 2009/0326660 A1 | 12/2009 | Abendschein | |
| 2009/0326670 A1 | 12/2009 | Keefer et al. | |
| 2010/0030339 A1 | 2/2010 | Berelsman et al. | |
| 2010/0145452 A1 | 6/2010 | Blaylock et al. | |
| 2010/0145466 A1 | 6/2010 | Slone | |
| 2010/0209666 A1* | 8/2010 | Rivard | A61F 2/30767 428/148 |
| 2010/0312349 A1 | 12/2010 | Berelsman et al. | |
| 2011/0009973 A1 | 1/2011 | Meyers et al. | |
| 2011/0009975 A1 | 1/2011 | Allen et al. | |
| 2011/0054628 A1 | 3/2011 | Banks et al. | |
| 2011/0093086 A1 | 4/2011 | Witt et al. | |
| 2011/0215930 A1 | 9/2011 | Lee et al. | |
| 2012/0022662 A1* | 1/2012 | Conway | A61B 17/8066 623/22.21 |
| 2012/0041564 A1* | 2/2012 | Landon | A61F 2/30734 623/20.34 |
| 2012/0135192 A1 | 5/2012 | Palmaz et al. | |
| 2012/0197415 A1* | 8/2012 | Montanari | A61F 2/0063 623/23.74 |
| 2013/0017232 A1* | 1/2013 | Varghese | A61K 35/12 424/400 |
| 2013/0131741 A1* | 5/2013 | Kourtis | A61F 2/4603 606/86 R |
| 2013/0211541 A1* | 8/2013 | Kerr | A61L 27/16 623/23.58 |
| 2014/0257517 A1* | 9/2014 | Deichmann | A61F 2/0063 623/23.74 |
| 2015/0012109 A1* | 1/2015 | Moreau | A61F 2/30771 623/23.43 |
| 2015/0335434 A1* | 11/2015 | Patterson | A61F 2/30767 623/23.5 |
| 2017/0056190 A1* | 3/2017 | Guilford | A61F 2/4202 |
| 2017/0196693 A1* | 7/2017 | Jurick | A61F 2/34 |
| 2018/0014938 A1* | 1/2018 | Hagen | A61F 2/3859 |
| 2019/0117827 A1* | 4/2019 | Roth | A61L 27/06 |

FOREIGN PATENT DOCUMENTS

| | | |
|---|---|---|
| CN | 101161294 A | 4/2008 |
| DE | 3119130 A1 | 3/1983 |
| DE | 4133433 C1 | 5/1993 |
| DE | 60115215 T2 | 8/2006 |
| EP | 0728448 A1 | 8/1996 |
| EP | 0827726 A2 | 3/1998 |
| EP | 0838286 A1 | 4/1998 |
| EP | 0846453 A2 | 6/1998 |
| EP | 1870060 A1 | 12/2007 |
| EP | 2145604 A1 | 1/2010 |
| EP | 2226408 A1 | 9/2010 |
| GB | 2057888 A | 4/1981 |
| JP | 05-200058 A | 8/1993 |
| JP | 2010-012254 A | 1/2010 |
| WO | 1998015240 A1 | 4/1998 |
| WO | 01/70136 A2 | 9/2001 |
| WO | 2004032806 A1 | 4/2004 |
| WO | 2004062531 A1 | 7/2004 |
| WO | 2009022911 A2 | 2/2009 |

OTHER PUBLICATIONS

Korean Office Action; Korean Intellectual Property Office; Korean Patent Application No. 10-2013-7000339; dated Jun. 21, 2017; 8 pages.

Korean Notice of Last Preliminary Rejection; Korean Intellectual Property Office; Korean Patent Application No. 10-2013-7000339; dated Aug. 7, 2018; 5 pages.

Chinese Office Action; Chinese Patent Office (State Intellectual Property Office of People's Republic of China); Chinese Patent Application No. 201180039345.2; dated Sep. 28, 2014.

Chinese Office Action; Chinese Patent Office (State Intellectual Property Office of People's Republic of China); Chinese Patent Application No. 201180039337.8; dated Jan. 18, 2016; 9 pages.

International Search Report and Written Opinion of the International Searching Authority; International Patent Application No. PCT/US2011/039658; dated Feb. 23, 2012.

Australian Examination Report; Australian Patent Office; Australian Patent Application No. 2016202986; dated Feb. 9, 2017; 3 pages.

Australian Examination Report; Australian Patent Office; Australian Patent Application No. 2011264852; dated Oct. 26, 2015; 4 pages.

European Examination Report; European Patent Office; European Patent Application No. 11793107.1; dated Nov. 15, 2017; 8 pages.

Korean Notice of Preliminary Rejection; Korean Intellectual Property Office; Korean Patent Application No. 10-2013-7000385; dated Aug. 22, 2017; 8 pages.

Korean Notice of Final Rejection; Korean Intellectual Property Office; Korean Patent Application No. 10-2013-7000339; dated Apr. 26, 2018; 8 pages.

Australian Examination Report; Australian Patent Office; Australian Patent Application No. 2016231485; dated Dec. 7, 2017; 5 pages.

European Examination Report; European Patent Office; European Patent Application No. 11793105.5; dated Nov. 7, 2017; 6 pages.

European Examination Report; European Patent Office; European Patent Application No. 11793109.7; dated Jan. 2, 2018; 6 pages.

(56) References Cited

OTHER PUBLICATIONS

Korean Second Final Rejection; Korean Intellectual Property Office; Korean Patent Application No. 10-2013-7000339; dated Mar. 20, 2019; 3 pages.
Examination Report for Indian Patent Application No. 10677/DELNP/2012, dated Jun. 28, 2019.
Examination Report for Indian Patent Application No. 10649/DELNP/2012, dated May 21, 2019.
Examination Report for Indian Patent Application No. 10676/DELNP/2012, dated Aug. 5, 2019.

* cited by examiner

IMPLANT COMPONENTS AND METHODS

CROSS REFERENCE TO RELATED APPLICATIONS

This application is a continuation of U.S. patent application Ser. No. 14/191,600, filed Feb. 27, 2014, which is a divisional of U.S. patent application Ser. No. 13/156,245, filed Jun. 8, 2011 and now issued as U.S. Pat. No. 8,700,198, which claims the benefit of U.S. Provisional Patent Application No. 61/352,705, filed Jun. 8, 2010, U.S. Provisional Patent Application No. 61/352,722, filed Jun. 8, 2010, U.S. Provisional Patent Application No. 61/422,903, filed Dec. 14, 2010, and U.S. Provisional Patent Application No. 61/466,817, filed Mar. 23, 2011, the contents of each application hereby incorporated by reference herein in their entireties.

BACKGROUND

Joints often undergo degenerative changes due to a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic material, typically metals, ceramics, or plastics.

More particularly, natural hips often undergo degenerative changes, requiring replacement of the hip joint with a prosthetic joint. Often, the hip is replaced with two bearing surfaces between the femoral head and the acetabulum. The first bearing surface is typically a prosthesis shell or acetabular cup, which may be formed of metal, ceramic material, or as otherwise desired. A liner (conventionally formed of polyethylene material such as ultra high molecular weight polyethylene, a ceramic material, or in some cases, even a metal liner) is then fit tightly within the shell to provide an inner bearing surface that receives and cooperates with an artificial femoral head in an articulating relationship to track and accommodate the relative movement between the femur and the acetabulum.

The cup (or a cup and liner assembly) is typically fixed either by placing screws through apertures in the cup or by securing the cup with cement. In some cases, only a liner is cemented in a patient due to poor bone stock. In other cases, a cup having a porous surface may be press fit into the reamed acetabular surface.

It may become necessary to conduct a second or subsequent surgery in order to replace a prosthetic joint with a (often larger) replacement joint. Such surgeries often become necessary due to further degeneration of bone or advancement of a degenerative disease, requiring removal of further cone and replacement of the removed, diseased bone with a larger or enhanced prosthetic joint, often referred to as a revision prosthesis. For example, bone is often lost around the rime of the acetabulum, and this may provide less rim coverage to securely place a press-fit cup. Such surgeries may thus be referred to as revision surgeries.

In acetabular revision surgery, an acetabular prosthesis generally includes additional mounting elements, such as augments, flanges, hooks, plates, or any other attachment or mounting points or members that provide additional support and/or stability for the replacement prosthesis once positioned. These additional mounting or attachment members are often required due to bone degeneration, bone loss, or bone defects in the affected area (in this instance, the hip joint).

Various types of these mounting members (which term is intended to include but not be limited to flanges, blades, plates and/or hooks) may be provided in conjunction with a prosthesis system in order to help the surgeon achieve optimal fixation, non-limiting examples of which include iliac flanges (providing securement and fixation in and against the ilium region of the pelvis), ischial blades (providing securement and inferior fixation by engaging the obturator foramen). Although there have been attempts to provide such mounting attachments with modularity, the solutions to date have generally fallen short of providing true modularity. Instead, they typically provide a few discrete positions at which the mounting members may be positioned, without providing the surgeon a fuller range of decision options.

Additionally, in some primary surgeries and more often in revision surgeries, the acetabulum may have a bone defect or void that the surgeon must fill with bone grafts before inserting a new shell. This can be time consuming and expensive, and may subject the patient to additional health risks. Some techniques use an augment in connection with the acetabular shell, which can be couples to or otherwise attached to the outer surface of the shell.

With current augments, the surgeon can attach the augment to the bone and then implant the cup. However, many acetabular shells rely on bone screws to achieve proper fixation and the augment often gets in the way of a screw. In short, surgeons need the freedom to place screws in the best location, but this compromises their ability to use augments. With current systems, it also takes an increased amount of time surgical time to trial the component orientation and then try to find good bone fixation for the cup. The surgeon will often have to free-hand the amount of bone removed while estimating the size of augment needed. In the cases where bone is often deficient, surgeons are hesitant to take away any more bone than necessary.

Various additional features and improved features intended for use and application with various types of joint implants are also described herein, such as improved bone screws, improved coatings, and various augment removal and insertion options.

SUMMARY

Disclosed herein are systems, devices, and methods for providing modular orthopedic implants. The implants may include a base member, such as an acetabular shell or an augment, that is configured to couple with an augment, flange cup, mounting member, any other suitable orthopedic attachment, or any combinations thereof. Mounting members include, for example, flanges, blades, hooks, and plates. In some embodiments, the orthopedic attachments may be adjustably positionable about the base member or other attachments thereby providing modularity for assembling and implanting the device. Various securing and/or locking mechanisms may be used between the components of the implant. In certain embodiments, the orthopedic attachments are removably coupled to the base member or other components. In certain embodiments, the orthopedic attachments are integrally provided on the base member or other components, yet may still be adjustably positionable thereabout. In some embodiments, expandable augments, base members, or other bone filling devices are provided. In some embodiments, surface features are provided that create friction and allow for surrounding bone ingrowth at the interface of the implants and a patient's bone.

Systems, devices, and methods described herein provide implants that create friction and allow for surrounding bone ingrowth at the interface of the implants and a patient's bone. In certain embodiments, an implantable orthopedic device includes an implant that has a surface that contacts a patient's joint and has a plurality of protrusions connected to the surface that rise above the surface. The implant may also include pores dispersed throughout the surface at the bone interface. The protrusions located at the surface of the implant may be blunt, or may be any other suitable shape and configuration. The protrusions may extend from the surface to any suitable height, such as heights between about 50 μm and about 2000 μm, heights between about 100 μm and 1100 μm, or heights between about 200 μm and 400 μm. The protrusions may be spaced on the surface of the implant in any suitable concentration or density. The desired protrusion density may also be patient-specific, and may be determined based on the density of a native bone into which a component is implanted. An implant may have a large number of protrusion features on its surface, and one or more of these individual features may fall outside of a desired size or spacing without affecting the overall efficacy of the surface.

In certain embodiments, an implant includes internal or external strengthening features A porous implant may include internal or external strengthening ribs to provide support to surrounding porous structures. A porous implant may also be coupled with a flange that has a first end for attaching the flange to the implant and a second end for attaching the flange to surrounding bone structure. The porous implant may also include a reticulated surface coating.

In certain embodiments, an implantable orthopedic device is created by providing a mold having a negative impression of a porous beaded surface and providing an implant substrate to be coated. Particles are interposed between the implant substrate and the mold, and a pressure or elevated temperature may be applied to the mold, implant substrate, and particles. The implant substrate provided may be solid or may be porous, and the particles interposed between the implant substrate and the mold may be symmetric or asymmetric.

In certain embodiments, an implantable orthopedic device is created by creating a three-dimensional model simulating an outer surface profile of a porous beaded implant and creating a three-dimensional model of an implant substrate volume. The model simulating an outer surface profile of a porous beaded implant is applied to the model of an implant substrate volume to create a pre-form volume, and an algorithm is applied to fill the pre-form volume with a desired reticulated structure to create a porous implant model. An implant is formed using the porous implant model.

In certain embodiments, an implantable orthopedic device is created by providing a mold of an implant having an inner surface mimicking a negative image of an outer surface profile geometry of a porous beaded surface and providing a plurality of particles that are placed into the mold. Pressure or elevated temperature is applied to the mold and particles. The particles placed into the mold may be symmetric or asymmetric.

In certain embodiments, an implantable orthopedic device is created by providing a mold of an implant having an inner surface mimicking a negative image of an outer surface profile geometry of a porous beaded surface and loading one or more foaming agents into the mold. A porous foam component is created in the general shape or size of the implant that has an outer surface geometry mimicking an outer surface profile geometry of a porous beaded surface. The porous foam component is removed from the mold, and a binding agent is applied to the porous foam component. A plurality of symmetric or asymmetric particles are applied to the porous foam component having the binding agent and the porous foam component, binding agent, and particles are subjected to an elevated temperature to sinter the particles together and burn out the foam component to form an implant having a roughened porous texture with an outer surface profile geometry mimicking a clinically-proven porous beaded structure. The porous foam component may be polymeric, and may be a polyurethane component.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

Figure 1:
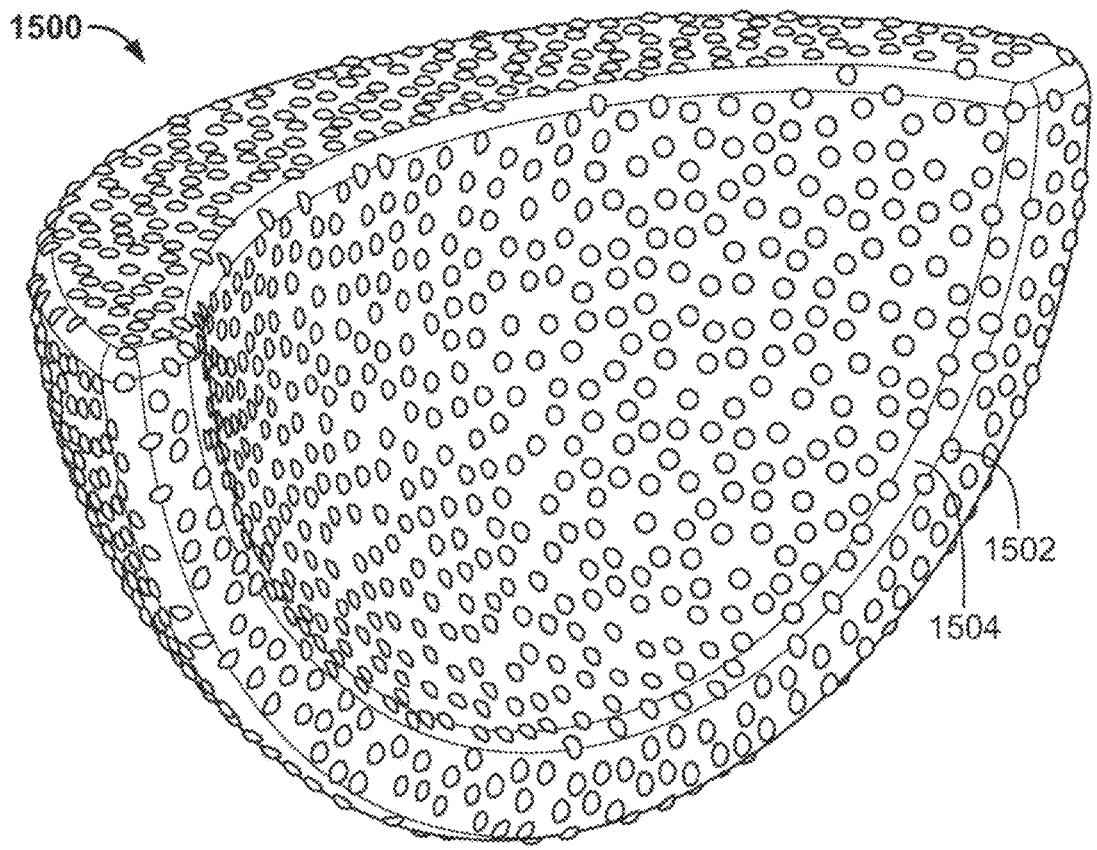
FIG. 1 shows a first view of an illustrative implant component.

To provide an overall understanding of the systems, devices, and methods described herein, certain illustrative embodiments will be described. Although the embodiments and features described herein are specifically described for use in connection with acetabular systems, it will be understood that all the components, connection mechanisms, adjustable systems, fixation methods, manufacturing methods, coatings, and other features outlined below may be combined with one another in any suitable manner and may be adapted and applied to medical devices and implants to be used in other surgical procedures, including, but not limited to: spine arthroplasty, cranio-maxillofacial surgical procedures, knee arthroplasty, shoulder arthroplasty, as well as foot, ankle, hand, and other extremity procedures.

Various implants and other devices described herein in their various embodiments may be used in conjunction with any appropriate reinforcement material, non-limiting examples of which include bone cement, appropriate polymers, resorbable polyurethane, and/or any materials provided by PolyNovo Biomaterials Limited, or any suitable combinations thereof. Further non-limiting examples of potential materials that may be used are described in the following references: U.S. Patent Application Publication No. 2006/0051394, entitled "Biodegradable Polyurethane and Polyurethane Ureas," U.S. Patent Application Publication No. 2005/0197422, entitled "Biocompatible Polymer Compositions for Dual or Multi Staged Curing," U.S. Patent Application Publication No. 2005/0238683, entitled "Biodegradable Polyurethane/Urea Compositions," U.S. Patent Application Publication no. 2007/0225387, entitled "Polymer Compositions for Dual or Multi Staged Curing," U.S. Patent Application Publication No. 2009/0324675, entitled "Biocompatible Polymer Compositions," U.S. Patent Application Publication No. 2009/0175921, entitled "Chain Extenders," and U.S. Patent Application Publication No. 2009/0099600, entitled "High Modulus Polyurethane and Polyurethane/Urea Compositions." Each of the prior references is incorporated by reference herein in its entirety.

Referring now to FIGS. 1-7, certain embodiments provide components having porous beaded coatings and methods for their manufacture. Because implants and natural bone usually have different degrees of flexibility, uneven stress distributions may occur. Consequently, when an implant is loaded, there is generally some relative movement at the interface between the bone (more compliant) and the implant (more rigid). Many implants thus employ an intermediate material such as bone cement to reduce the amount of relative movement; however, cementless implants may rely on relative roughness to achieve the same goals.

Historically, small spherical beads, bundles of thin wires, and thermal-sprayed metal have been used to produce the friction necessary to reduce the amount of relative movement. Optionally, screws and/or press-fit features may improve the fixation of implant to bone. Such technologies are generally accepted by the orthopedic surgeon community. However, the geometric nature of these coatings limits the location and size of their porosity. Newer technologies, such as those that employ asymmetric beads or metallic foams have improved the location and size of porosity, but they are difficult to manufacture with favorable surface textures. Remedies have included placing hatch lines into the surface of an already porous coating (e.g., via machining). Other porous surfaces have been manufactured having sharp protrusions at a microscopic level. These protrusions can cause problems when there is even a small amount of relative movement between the bone and implant. The sharper protrusions can dig into the bone and create bone particles or can break off from the implant and create wear particles at the implant-bone interface. In addition to loosening the attachment between the implant and bone, these loose particles can cause harmful complications.

The shortcomings of previous porous surfaces are addressed by providing an implant having a surface that is textured with numerous blunt protrusions on a macroscopic level and has a porous structure on a microscopic level. The blunt protrusions create friction that reduces the amount of relative movement between an implanted component and surrounding bone. The porosity allows the surrounding bone to grow into the implant, and the lack of relative movement between implant and bone facilitates this ingrowth.

A consideration in designing and creating a porous implant having blunt protrusions is the size and density of the protrusions. The protrusions create an area on which the bone initially contacts an implant. If the protrusions are too large or spaced too far apart, the majority of the implant's surface area between the protrusions will be too far from the bone for the bone to grow into the implant, and the bone may be unable to create a solid interface with the implant. In contrast, if the protrusions are too small or located too close together, their effect will be minimal and an implant may encounter the same problems as prior implants with smoother surfaces or surfaces composed of many concentrated sharp protrusions. An ideal surface contains protrusions that are large enough to create the needed friction between the bone and implant and still small enough to still allow for a high degree of bone ingrowth into the porous surface. The protrusions may be any suitable height, and preferably are between about 50 µm and about 2000 µm. For certain applications, it may be preferable to limit the protrusion heights to between 200 µm and 400 µm to achieve the desired level of friction and ingrowth with surrounding bone.

Protrusions on a surface of an implantable component may be any suitable shape or profile desired for a general or specific application of the component. In certain embodiments, each surface protrusion may be a bump shaped as a portion of a sphere above the surface of the implant. Protrusions may also be shaped like wires or any other suitable features, including features common to cementless implants.

Figure 2:
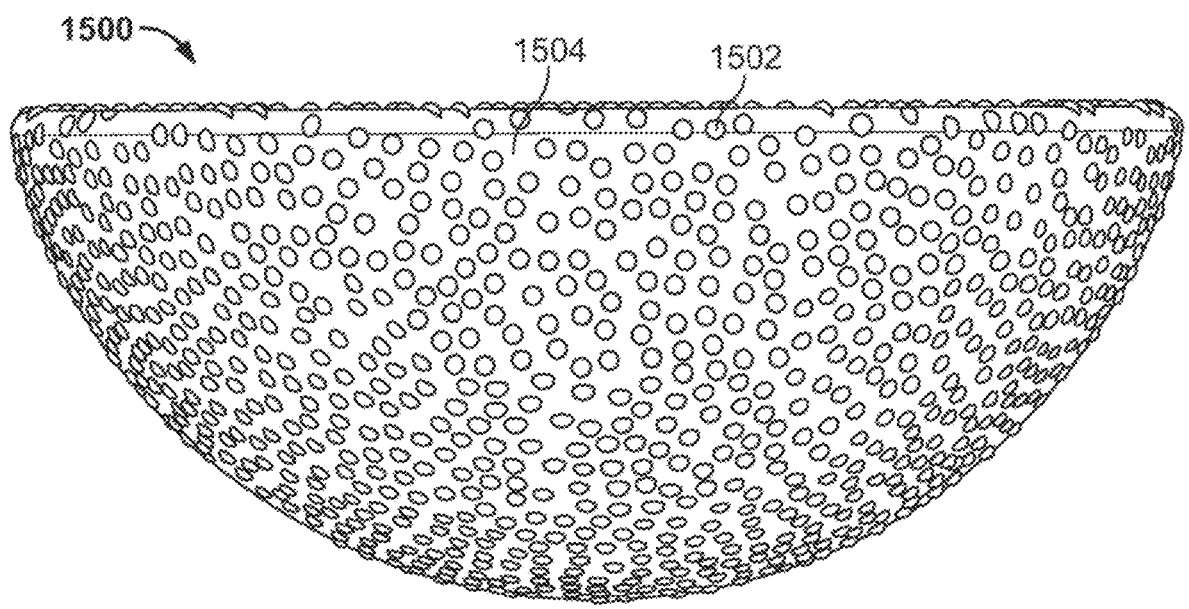
FIG. 2 shows a second view of an illustrative implant component.

FIGS. 1 and 2 show some embodiments of an improved acetabular implant 1500 which may be a whole augment, a portion of an augment, a flange, a plate, other mounting member, a shell, or a cage. The improved acetabular implant 1500 mimics the bumpy outer surface geometrics and profiles of clinically-successful porous beads, with the roughness and porosity of a desired ingrowth interface. The surface of implant 1500 is textured by blunt protrusions 1502, which are shaped substantially as hemispherical bumps on the surface of implant 1500. The protrusions 1502 are sized and spaced to create desirable friction that reduces movement of the implant 1500 relative to surrounding bone while allowing the surrounding bone to grow substantially into the porous protrusions 1502 and porous surface area 1504 between the protrusions. In addition to the protrusion heights discussed above, the spacing and density of protrusions 1502 affect the amount of friction and bone ingrowth created. Any suitable density of protrusions 1502 may be used for an implant, and the protrusions preferably occupy between about 10% and about 60% of the surface. The protrusions may be concentrated to a density of between about 0.25 beads/mm$^2$ and about 6 beads/mm$^2$.

Improved acetabular implants, such as the implant 1500 of FIGS. 1 and 2, may be formed by any suitable approach, and may be formed using one of the following four methods.

A first method includes the steps of: 1) providing a mold having a negative impression of a porous beaded surface, 2) providing an implant substrate, which may be solid or porous, to be coated, 3) interposing small asymmetric particles between the implant substrate and said mold, and 4) applying a pressure and/or an elevated temperature to the mold, implant substrate, and small asymmetric particles to create a "green-state" implant (i.e., ready for full sintering) or a final implant (sintered), the implant having a roughened porous coating with an outer surface geometrics and profiles mimicking a clinically-proven porous beaded structure with the roughness and porosity of a desired trabecular structure.

A second method includes the steps of: 1) creating a 3D model simulating an outer surface profile of a porous beaded implant, 2) creating a model of an implant substrate volume, 3) applying the 3D model simulating an outer surface profile of a porous beaded implant to the 3D model of the implant substrate volume to create a bumpy pre-form volume, 4) applying an algorithm to fill the bumpy pre-form volume with a desired interconnected porous or otherwise reticulated structure to create a porous implant model, and 5) creating an implant having a roughened porous texture with an outer surface profile geometry mimicking a clinically-proven porous beaded structure using the implant model in a rapid-manufacturing process.

A third method includes the steps of: 1) providing a mold of an implant having an inner surface mimicking a negative image of an outer surface profile geometry of a porous beaded surface, 2) providing a plurality of small asymmetric particles, 3) placing the plurality of small asymmetric particles into the mold, and 4) applying a pressure and/or an elevated temperature to the mold and/or small asymmetric particles to create a "green-state" implant (i.e., ready for full sintering) or a final implant (sintered), the implant having a roughened porous texture with an outer surface profile geometry mimicking a clinically-proven porous beaded structure.

A fourth method includes the creation of a beaded surface on a foam component during the precursor step of making a metallic foam, the method comprising the steps of: 1) providing a mold of an implant having an inner surface mimicking a negative image of an outer surface profile geometry of a porous beaded surface, 2) loading one or more foaming agents into the mold, 3) creating a porous foam component (e.g., polymeric, polyurethane) in the general shape and/or size of said implant, which has an outer surface geometry mimicking an outer surface profile geometry of a porous beaded surface, 4) removing the porous foam component from the mold, 5) applying a binder or binding agent to the porous from a component, 6) applying a plurality of small symmetric or asymmetric particles (or a combination thereof) to the porous foam component having a binder or binding agent thereon, 7) subjecting the porous foam component having binder or binding agent and particles thereon to an elevated temperature to sinter the particles together and/or burn out the foam component to form a "green-state" implant (i.e., ready for full sintering) or a final implant (sintered), the implant having a roughened porous texture with an outer surface profile geometry mimicking a clinically-proven porous beaded structure. Implant has a bumpy outer surface profile and geometrics mimicking a clinically-proven porous-beaded structure.

The substrate forming at least an outer portion of the implant may be a bulk porous, reticulated structure resembling a trabecular structure. One or more core portions or outer surface portions of the implant may be solid (e.g., a portion of the implant may be configured for articulation with another implant component). The implant may also include one or more solid internal portions. For example, implant 1500 shown in FIG. 1 may include a solid structural portion on the interior of the implant. The structural portion may be a single solid area or multiple solid areas on the interior of implant 1500 that provide a series of structural ribs to add support to the implant. The solid internal structure may have any suitable shape and configuration, such as a structural lattice similar to rebar in concrete. Illustrative but non-limiting examples areas where the internal structure may be desired include areas around screw holes, the equator region of an augment, or any other suitable area. In some embodiments, a polymer foam could be melted or burned to have the shape of beads—or the foam could be polymerized on a bead-shaped subsurface resulting in the end-product having a bead-shaped surface. In addition to solid internal components, implant 1500 may be coupled with external flanges or other mounting members to provide additional support to the implant. For example, implant 1500 may be implanted along with a flange that is attached to the implant at a first end of the flange and attached to a patient's bone at a second end, for example, with a bone screw secured into a through-hole in the flange. Implant 1500 may also include external solid reinforcements, similar to common strut and brace structures, to provide support to porous sections of the implant.

For rapid-manufacturing technologies, the bead surface geometrics and profile could be created virtually and subtracted out from a bulk porous entity or virtual beads could be created and combined with a porous entity. It is the general intent, in some, but not necessarily all, embodiments that the end-product be homogenous. Alternate embodiments of implants may include surface profiles that mimic metallic wire bundles or the peaks and valleys of a thermal sprayed coating. Once a virtual model of the desired geometry is created using modeling software, an implant component having the desired surface profile can be created using any suitable rapid manufacturing techniques. For example, the porous implant can be created using 3D printing technology that uses powdered metal to "print" the modeled implant. In such an approach, a foam may be created having a surface profile that includes protrusions, such as protrusions 1502 in FIGS. 1 and 2, and the profiled foam may then be filled in with powdered metal to create a porous microstructure with the profiled surface. A foam that does not contain the protrusions may also be used to create the porous microstructure with powdered metal, and the desired surface profile with protrusions can then be stamped into the surface of the porous metal implant.

Advantages of implants manufactured this way are that they contain integral porosity with the initially bone-engaging surface profile of clinically-proven porous beads. In other words, the same features providing the traction needed between bone and implant are the same features providing a surface for bone to grow into and around for a rigid and enduring fixation surface. As non-limiting examples, Tables A and B show some examples of potentially suitable bead density (spacing), and diameter.

TABLE A

Chart of number of beads in selected area and average and standard deviation of bead diameter of 50 beads on a shell used with the Birmingham Hip ® Resurfacing system available from Smith & Nephew, Inc. in at least 3 fields of view (SEM, Jeol, Japan)

| Beads in 6.4 × 4.8 mm area | Bead Diamter (mm) | |
|---|---|---|
| 11 | Average D | 1.24 |
| 20 | Std D | 0.12 |
| 20 | | |

TABLE B

Percent solid for typical beaded product for bone ingrowth.

| Product | Company | Implant Type | Percent Solid |
|---|---|---|---|
| CoCr ROUGHCOAT (2-layer) | Smith and Nephew | Profix ® Femoral | 46.3% |
| CoCr Porocoat (3-layer) | DePuy | LCS ® Knee Femoral | 46.5% |
| CoCr Porocoat (3-layer) | DePuy | AML ® Stem | 50.2% |
| Ti ROUGHCOAT (2-layer) | Smith and Nephew | Synergy ™ Stem | 51.9% |

Wherein, "percent solid" is a 2D measurement of bead density produced by typical metallographic techniques based on the test method disclosed in ASTM F1854, entitled "Standard Test Method for Stereological Evaluation of Porous Coatings on Medical Implants," which is incorporated by reference herein in its entirety.

Figure 3:
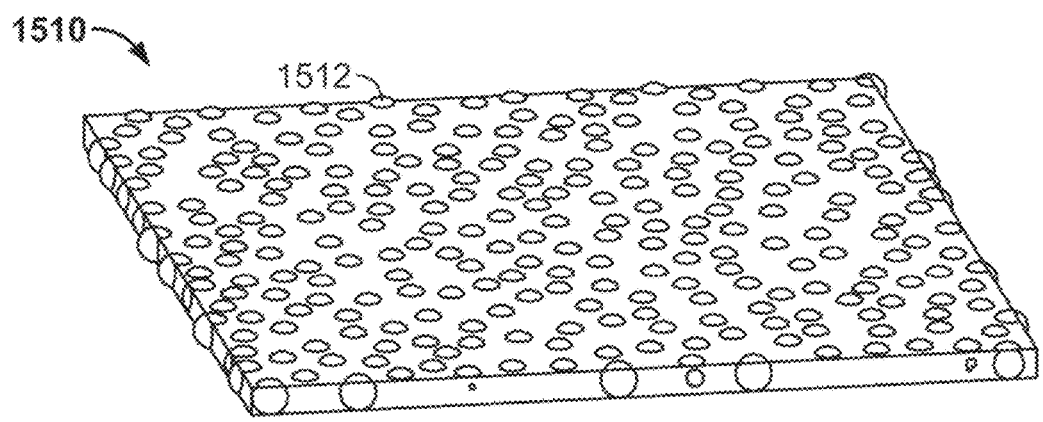
FIG. 3 shows an illustrative implant coating volume having a spherical bead surface profile.

FIG. 3 shows a coating volume 1510 having spherical bead volumes 1512 placed therein, such that the spherical bead volumes 1512 protrude from the coating volume 1510 to form a second coating volume mimicking a spherical bead profile. Alternatively, solid spherical beads may be combined into a porous coating. To create the coating volume 1510, two software models can be created and then merged to form the final model of the porous volume with the profiled protrusion surface. A first model of a macroscopic structure of the volume, including the plurality of bead volumes 1512, can be created in modeling software, and may look substantially the same as the volume shown in FIG. 3.

Figure 4:
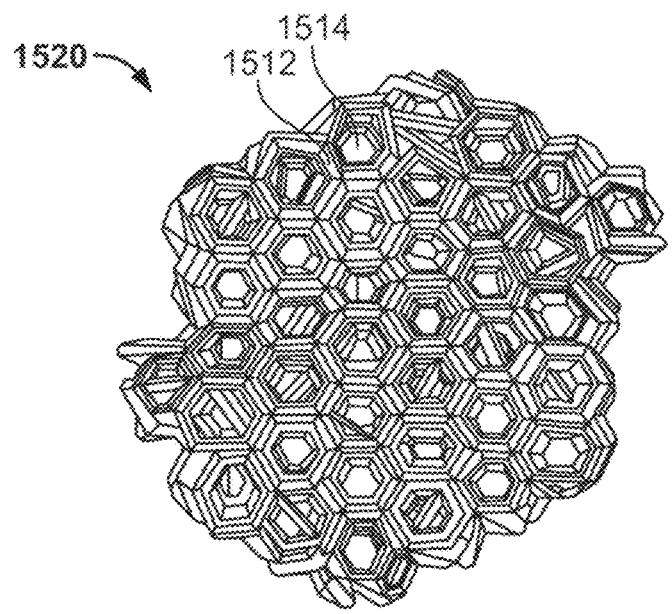
FIG. 4 shows an illustrative unit cell having a porous structure.

A second software model can be created to produce the porous microscopic structure desired for a macroscopic volume, such as the volume shown in FIG. 3. FIG. 4 shows a unit cell 1520 of an exemplary porous reticulated structure, which may configured to fill the coating volume mimicking a spherical bead profile. The unit cell 1520 is made up of a complex structure of struts 1512. The arrangement of struts 1512 creates voids 1514 within unit cell 1520, thus making the desired porous microstructure. The size and arrangement of struts 1512 can be varied to control the number and size of voids 1514. By controlling the size and arrangement of the struts 1512, a desired amount and profile of the porous structure is achieved.

Figure 5:
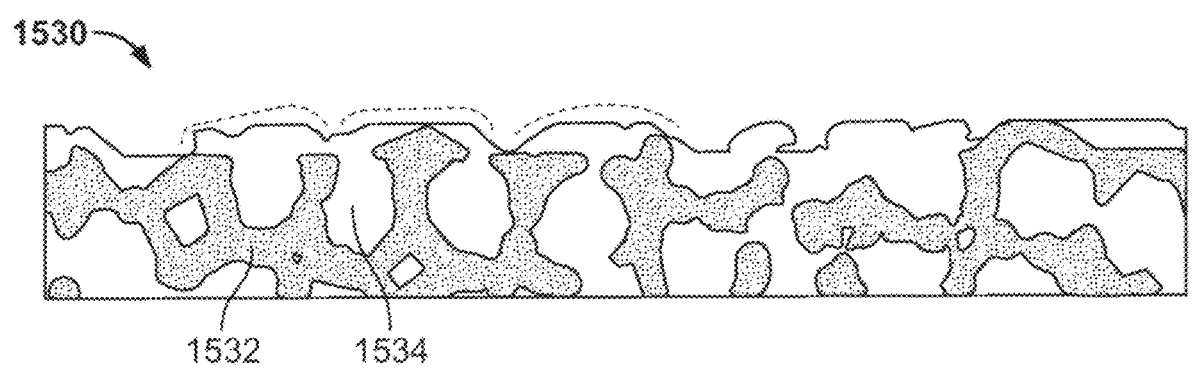
FIG. 5 shows a cross-section of an illustrative coating volume with a spherical bead profile and a porous structure.

FIG. 5 shows a cross section of a coating volume 1530, which may correspond to coating volume 1510 of FIG. 3, mimicking a spherical bead profile after the volume has been replaced with a reticulated structure (e.g., via a repeating unit cell such as unit cell 1520 in FIG. 4 in CAS software, or using any of the 4 methods described above). The finished coating volume 1530 exhibits both the profiled macrostructure and porous microstructure. The dotted lines in FIG. 5 outline the surface profile of coating volume 1530 and show the protrusions that create a bumpy surface that produces friction with bone when implanted. The microstructure of coating volume 1530, made up of a combination of solid structure 1532 and voids 1534, creates a porous implant into which surrounding bone can grow to fill in voids 1534 and create a solid mating of implant and bone.

Figure 6:
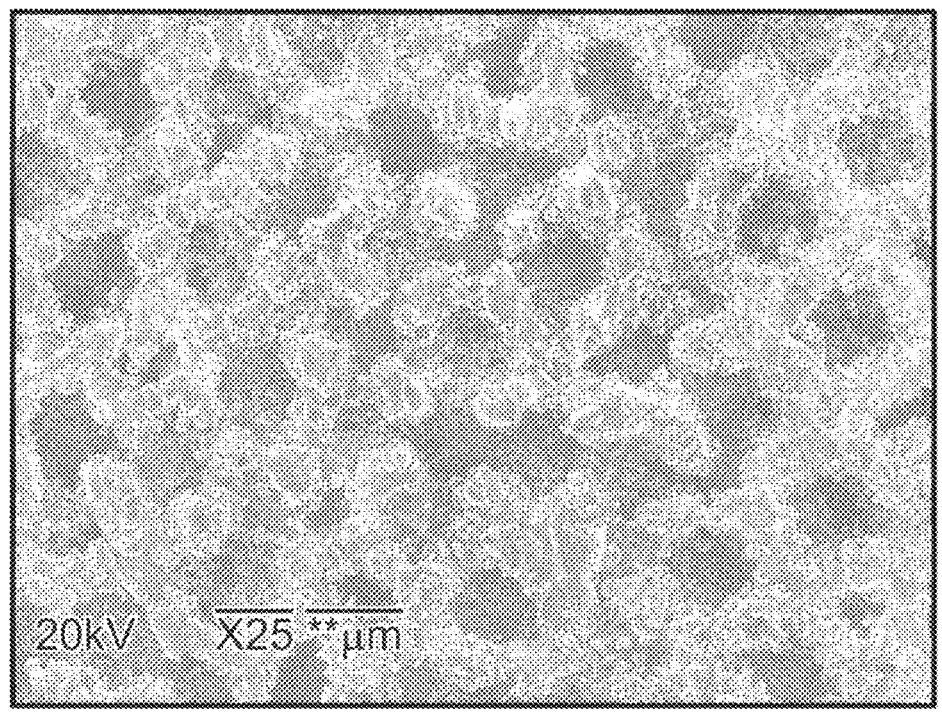
FIG. 6 shows a first illustrative SEM image of a porous surface.
Figure 7:
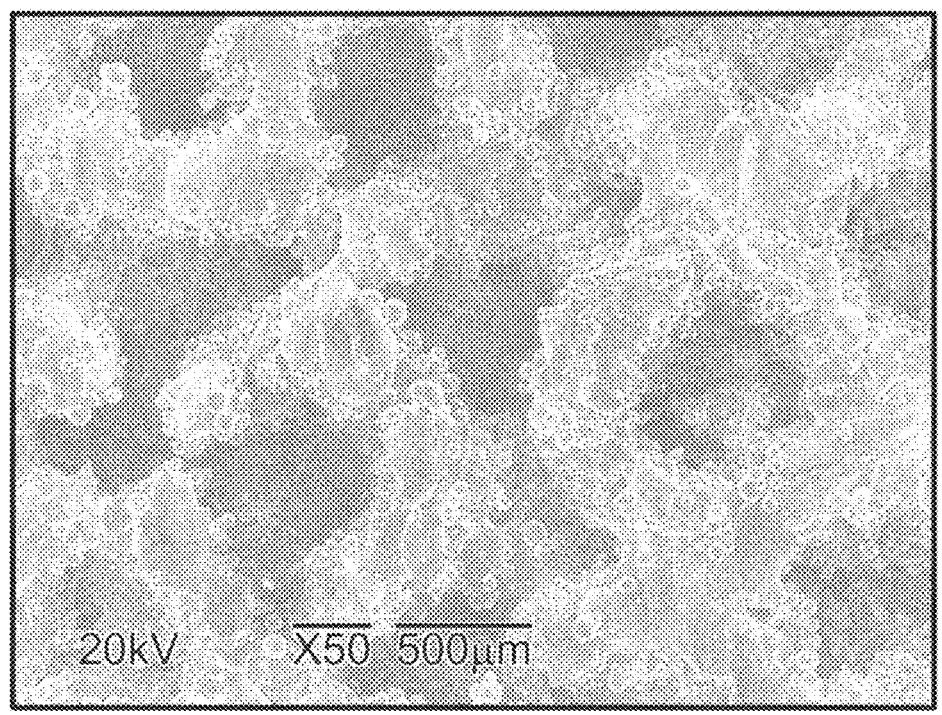
FIG. 7 shows a second illustrative SEM image of a porous surface.

FIG. 6 shows an SEM image 1540 taken at 25× magnification of the surface of a part made by the disclosed method. Surface topography is not apparent with this view. FIG. 7 is an SEM image taken 1550 at 50× magnification of the structure made with the disclosed method. The structures shown in FIGS. 6 and 7 exhibit the porous microstructure discussed above with respect to coating volumes 1510 and 1530, and can be created by merging a solid macrostructure with a porous microstructure model, such as the unit cell 1520 in FIG. 4.

As a further non-limiting example, the following chart shows some additional exemplary parameters that have proven to be useful for various embodiments. In the chart below, MVIL refers to Mean Void Intercept Length, which is another way of characterizing the average pore size, particularly in structures where the pore shapes and sizes are not uniform. On generally known definition of MVIL is "measurement grid lines are oriented parallel to the substrate interface. The number of times the lines intercept voids is used with the volume percent void to calculate the mean void intercept length."

|  |  | Electron beam melting (EBM) | Direct metal laser sintering (SLS) Eurocoating EOS | Landon Structure (FIG. 4) |
| --- | --- | --- | --- | --- |
| Avg. Strut Thickness (μm) |  | — | 275-450 (360) | 275-400 (340) |
| Avg. Pore Size: MVIL |  | 300-920* (565) | 450-690 (560) | — |
| Average Pore Size: (μm) | Pore | 900-1300* | 1310 ± 280 | 1970 ± 40 |
|  | Window | — | 370 ± 100 | 830 ± 150 |
|  | Not Specified | 670-1340 | 600 ± 100 | — |

*(fine, medium, and coarse structures)

It is generally desirable to provide between about 60-85% porosity. Pore sizes may generally range between about 50-1000 microns. In the above example, the smallest pore size provided was about 300 microns, and the smallest window was about 595 microns across at its largest diameter. It will be understood that this example is intended to be non-limiting and provided for illustrative purposes only.

The systems, methods, and devices described herein to create implants having both a profiled macrostructure and a porous microstructure cart allow a medical professional to utilize customizable, patient-specific implants. A customized implant can be efficiently created using the rapid manufacturing techniques discussed herein by merging two or more models of an implant and then printing the modeled component. This could allow a medical professional, such as an orthopedic surgeon, to order an implant specific to a single patient, including modeling the size and shape of the implant to fit defects or other unique features of the patient's anatomy. This process can also be automated by taking bone scans of the patient's anatomy or using other available medical imaging and modeling techniques to automatically create a 3D model to use for rapid manufacturing.

The ability to customize an individual implant also allows a medical professional to adjust the detailed macrostructure and microstructure of the implant to fit the needs of a particular application. For example, an orthopedic surgeon can adjust the macrostructure of the implant by selecting the shape, height, density, or other characteristics of protrusions on the surface of the implant. The surgeon can also customize the number and size of voids within the implant to achieve a desired porosity for the implant. In some embodiments, the surgeon may also select the configuration of the macrostructure of the implant. For implants that include internal solid portions for strength and structure, the surgeon can customize the size and location of the internal solid portions to provide the structure in certain non-uniform areas of the implant where increased strength is needed. Illustrative but non-limiting examples where increased strength may be desired include areas around screw holes, the equator region of an augment, connection sites of augments, augment areas that are thinner than others, or any other suitable area. The surface profile of the implant can also be non-uniform if different areas of the implant require different levels of friction or surface area for a bone interface. A surgeon may want a higher concentration of surface protrusions in certain areas of the implant, such as area that experience higher levels of stress, and a lower concentration of protrusions, or not protrusions at all, in other areas.

Porous implants described herein allow for an implant to provide good contact surface area and friction regardless of the quality of bone into which an implant is implanted. For example, patients, who have soft spongy bone may need features that are longer, and a lower number of those features. Patients with hard dense bone may require features that are shorter, but a higher number of those features to create the same fixation in the bone. The specific requirements of a patient's anatomy and bone quality can be accommodated by the individualized design options provided by the porous implants described herein.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to medical devices to be used in other surgical procedures including, but not limited to, spine arthroplasty, cranio-maxillofacial surgical procedures, knee arthroplasty shoulder arthroplasty, as well as foot, ankle, hand, and extremities procedures.

Variations and modifications will occur to those of skill in the art after reviewing this disclosure. The disclosed features may be implemented, in any combination and subcombinations (including multiple dependent combinations and subcombination), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. An implantable orthopedic device, comprising:
   an implant having a porous surface defining a plurality of pores sized to accommodate bone-ingrowth into the implant, the implant further including a plurality of protrusions extending from the porous surface and which rise above the porous surface;
   wherein the plurality of protrusions has a concentration between about 0.25 protrusions per square millimeter and about 6 protrusions per square millimeter; and
   wherein the plurality of protrusions are configured to frictionally engage a bone surface without interfering with bone ingrowth into the plurality of pores.

2. The device of claim 1, wherein the protrusions are blunt.

3. The device of claim 2, wherein the protrusions comprise rounded protrusions extending from the porous surface.

4. The device of claim 3, wherein the rounded protrusions are hemispherical.

5. The device of claim 1, wherein the protrusions rise above the porous surface to a height between about 50 μm and about 2,000 μm.

6. The device of claim 5, wherein the height is between about 100 μm and about 1,100 μm.

7. The device of claim 6, wherein the height is between about 200 μm and about 400 μm.

8. The device of claim 1, further comprising a strengthening rib disposed along or within the implant.

9. The device of claim 8, further comprising a flange having a first end attached to the implant, and a second end that includes a through-hole for attachment to a patient's bone.

10. The device of claim 9, further comprising a reticulated surface coating on the implant.

11. The device of claim 1, wherein the implant comprises a solid non-porous portion.

12. The device of claim 11, wherein the solid portion of the implant comprises a solid external surface.

13. The device of claim 12, wherein the implant is configured to articulate with a second implanted component, and the solid external surface is configured to contact the second implanted component.

14. The device of claim 12, wherein the implant is an orthopedic augment, and the solid external surface comprises an augment connection site.

15. The device of claim 11, wherein the solid portion of the implant comprises a solid interior portion disposed within porous portions of the implant.

16. The device of claim 15, wherein the solid interior portion comprises a structural rib disposed within the interior of the implant.

17. The device of claim 11, wherein the implant comprises a screw hole, and the solid portion of the implant comprises a solid portion disposed around the screw hole.

18. The device of claim 11, wherein the solid portion of the implant comprises at least one of a solid portion disposed in the equator region of the implant and a solid portion disposed in an area of the implant that is thinner than other areas of the implant.

19. The device of claim 1, wherein the plurality of protrusions are integrally formed with the porous surface.

20. An implantable orthopedic device, comprising:
    an implant having a porous surface defining a plurality of pores sized to accommodate bone-ingrowth into the implant, the implant further including a plurality of rounded protrusions extending from the porous surface and which occupy approximately 10% to approximately 60% of the porous surface; and
    wherein the protrusions are configured to frictionally engage a bone surface without interfering with bone ingrowth into the plurality of pores.

21. The device of claim 20, wherein the pores have a size of approximately 50 microns to 1000 microns.

22. The device of claim 20, wherein the protrusions rise above the porous surface to a height between about 50 μm and about 2,000 μm.

23. The device of claim 22, wherein the height is between about 200 μm and about 400 μm.

24. The device of claim 20, wherein the protrusions comprise rounded hemispherical protrusions extending from the porous surface.

25. The device of claim 20, wherein the plurality of rounded protrusions has a concentration between about 0.25 protrusions per square millimeter and about 6 protrusions per square millimeter.

26. The device of claim 20, wherein the porous surface and the plurality of rounded protrusions form a single homogenous structure.

27. An implantable orthopedic device, comprising:
an implant having a porous surface defining a plurality of pores sized to accommodate bone-ingrowth into the implant, the implant further including a plurality of blunt protrusions extending from the porous surface and which occupy approximately 10% to approximately 60% of the porous surface;
  wherein the pores have a size of approximately 50 microns to 1000 microns;
wherein the protrusions rise above the porous surface to a height between about 50 microns and about 2,000 microns; and
wherein the protrusions are configured to frictionally engage a bone surface without interfering with bone ingrowth into the plurality of pores.

28. The device of claim 27, wherein the plurality of blunt protrusions has a concentration between about 0.25 protrusions per square millimeter and about 6 protrusions per square millimeter.

29. The device of claim 27, wherein the porous surface and the plurality of blunt protrusions define a single-piece contiguous structure.

\* \* \* \* \*